US00PP12847P2

(12) United States Plant Patent
Silveira

(10) Patent No.: US PP12,847 P2
(45) Date of Patent: Aug. 13, 2002

(54) AZALEA PLANT NAMED 'SWEET SIXTEEN'

(75) Inventor: Michael J. Silveira, Barrington, RI (US)

(73) Assignee: CP (Delaware), Inc., Wilmington, DE (US)

( * ) Notice: Subject to any disclaimer, the term of this patent is extended or adjusted under 35 U.S.C. 154(b) by 6 days.

(21) Appl. No.: 09/610,223

(22) Filed: Jul. 3, 2000

(51) Int. Cl.[7] ..... A01H 5/00
(52) U.S. Cl. ..... Plt./239

(58) Field of Search ..... Plt./239

*Primary Examiner*—Bruce R. Campell
*Assistant Examiner*—Annette H. Para

(57) ABSTRACT

A new and distinct Azalea cultivar is provided that abundantly forms clusters of sturdy double pearl pink hose-in-hose blossoms that commonly retain their attractive appearance even in inclement weather. The dark green and plentiful foliage substantially retains its coloration throughout the winter. The growth habit is dense, well-branched, and naturally mounding. The cultivar exhibits excellent hardiness and is tolerant to wet soils and clay soils.

3 Drawing Sheets

SUMMARY OF THE INVENTION

Figures 4, 5, 6, 7:
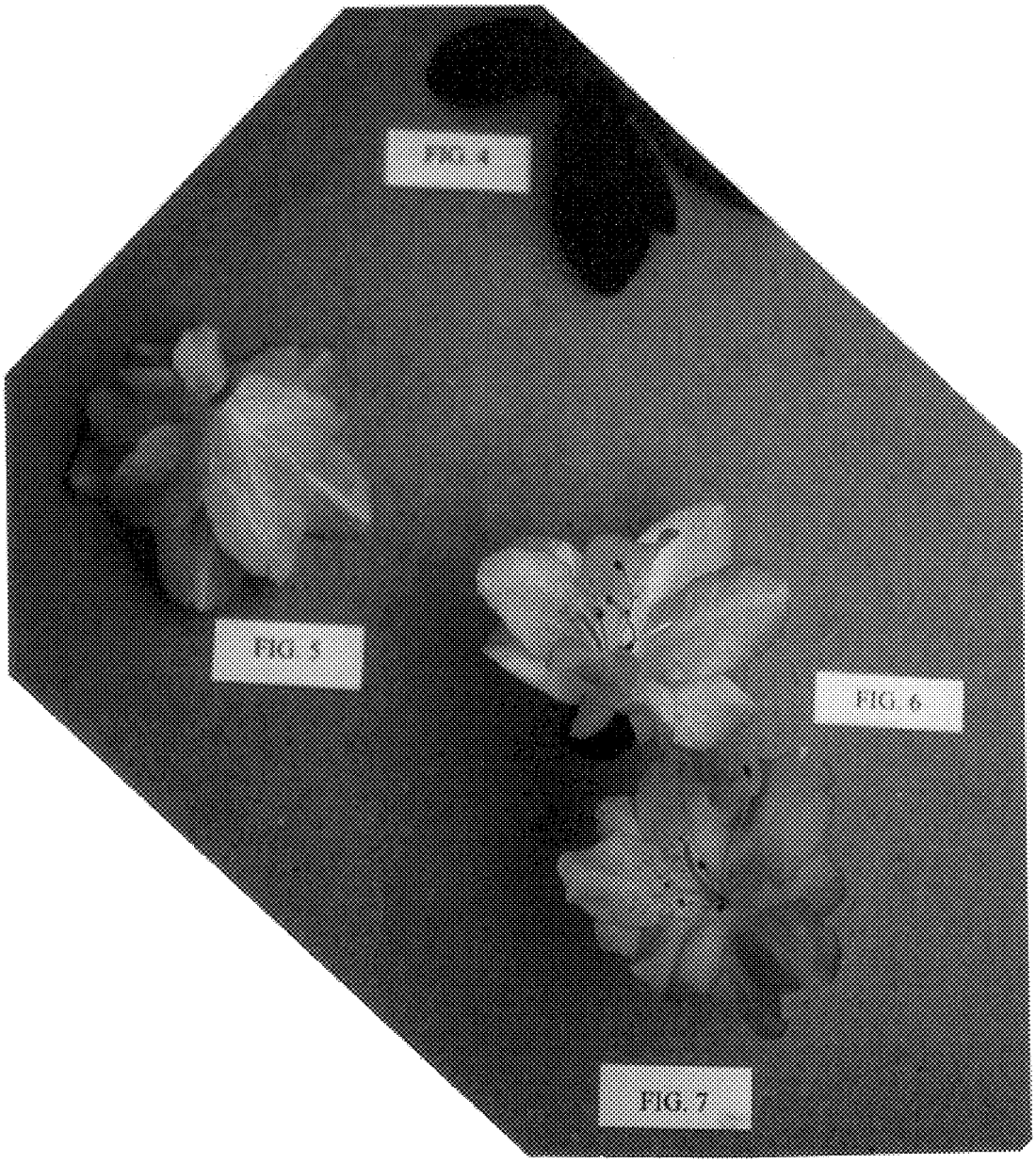

The new Azalea cultivar of the present invention was discovered in a garden at Barrington, R.I., as a natural hybrid cross. It is believed to be a hybrid of *Rhododendron yedoense poukhanense* resulting from open pollination in a mixed planting of *Rhododendron yedoense poukhanense* cultivars. The exact parentage of the new cultivar is unknown. The selection of the present invention was found growing among primarily 'Rosebud' (non-patented in the United States), 'Hino Crimson' (non-patented in the United States) and Mother's Day (non-patented in the United States) Azalea seedlings. It was an objective to discover an attractive cold hardy *poukhanense* Azalea that is at least equal in hardiness to the Girard Azalea hybrids.

It was found that the new cultivar of the present invention possesses the following combination of characteristics:

(a) Forms sturdy and attractive clusters of double pearl pink hose-in-hose blossoms, (b) Forms dark green foliage on a plentiful basis that generally retains its coloration in the winter, (c) Forms a dense well-branched naturally mounding growth habit, (d) Exhibits excellent bud hardiness, and (e) Exhibits tolerance to wet soils and clay soils.

Had the new cultivar of the present invention not been discovered and preserved by me it would have been lost to mankind.

The new cultivar can be grown in at least U.S.D.A. Hardiness Zone Nos. 5 to 8. For instance, good hardiness has been confirmed to date at Augusta, Me.; Lebanon, Conn.; and West Grove, Pa. The dark green foliage densely covers the branches. The attractive pearl pink blossoms contrast nicely with the dark green foliage. The retention of the dark green foliage coloration during the winter provides an attractive overall plant appearance throughout the year. The new cultivar does well in full-sun and half-sun growing conditions. The substantial tolerance to less than ideal soils, such as damp or clay soils, also broadens the usefulness of the new cultivar.

At five years of age the new cultivar commonly acheives a height of approximately 2½ feet and width of approximately 3 feet. At full maturity these dimensions each are increased by approximately one foot.

The new cultivar well meets the needs of the horticultural industry. It is particularly well suited for growing as distinctive and attractive ornamentation in the landscape. For instance, it can be grown to advantage as a foundation, mass, or specimen planting.

The new cultivar has been found to undergo asexual propagation by the rooting of cuttings at Barrington, R.I., and at West Grove, Pa. This asexual propagation has demonstrated that the unique combination of characteristics of the new cultivar is well established and is strictly transmissible from one generation to another.

The new cultivar of the present invention has been named 'Sweet Sixteen'.

BRIEF DESCRIPTION OF THE PHOTOGRAPHS

The accompanying photographs show as true as it is reasonably possible in color illustrations of this nature, plant parts of the new cultivar of the present invention. The plants were approximately five years of age and were photographed during May while growing outdoors at West Grove, Pa.

FIG. 1—illustrates a specimen of a typical branch with mature dark green as well as juvenile foliage;

FIG. 2—illustrates a specimen of the upper surface of a typical leaf;

FIG. 3—illustrates from above a specimen of a typical open blossom;

FIG. 4—illustrates a specimen of a typical branch with mature leaves and flower buds;

FIG. 5—illustrates from below a specimen of a typical open blossom;

FIG. 6—illustrates from above an additional specimen of an open blossom wherein the typical variation in pink blossom coloration is illustrated;

FIG. 7—illustrates from above a further specimen of an open blossom; and

FIG. 8—illustrates a specimen of a typical flowering branch bearing clusters of the attractive pink blossoms.

FIGS. 4 (portion) and 5, 6, and 7 are enlarged and are presented in an additional photograph. Also, FIG. 8 is enlarged and is presented in a further photograph.

DETAILED DESCRIPTION

The chart used in the identification of colors is that of The Royal Horticultural Society, London (R.H.S. Colour Chart). Other references to color are to be accorded their ordinary dictionary significance. The description is based upon the observation of seven year-old plants growing in containers at West Grove, Pa. The plants were present in a greenhouse covered with 25 percent shade cloth during the summer and white polyethylene sheeting during the winter.

Botanical classification: *Rhododendron poukhanense*, cv. 'Sweet Sixteen'.

Parentage: Seedling of unknown parentage. The new cultivar was discovered while growing in a garden containing mixed *poukhanense* seedlings.

Plant characteristics:

*Form.*—Naturally mounded, globular, dense, and well-branched.

*Size.*—The spread is approximately 90 cm and the height is approximately 70 cm.

*Branches.*—The length is approximately 15 cm, the diameter is approximately 2 to 3 mm, the color is near Greyed-Green Group 197A, and texture is slightly peeling.

Foliage characteristics:

*Arrangement.*—Alternate along the stem, and whirled at the base of the flower.

*Length.*—Approximately 3.4 to 4.8 cm when mature along the current season's growth. The leaves associated with the flower buds are considerably smaller.

*Width.*—Approximately 1.4 to 2.3 cm when mature along the current season's growth.

*Shape.*—Elliptic.

*Apex.*—Obtuse/mucronate.

*Base.*—Cuneate.

*Margin.*—Entire.

*Texture.*—Smooth with slight pubescence on both surfaces.

*Young foliage.*—Green Group 143C on the upper surface, and Yellow-Green Group 144C on the under surface.

*Mature foliage.*—Dark green, Yellow-Green Group 147A on the upper surface, and Yellow-Green Group 147C on the under surface. The venation is Yellow-Green Group 147C on the upper surface and Yellow-Green Group 147B on the under surface.

*Petiole.*—Approximately 5 mm in length, approximately 1 to 1.2 mm in diameter, and Yellow-Green Group 144C in coloration.

Flower characteristics:

*Flowering season.*—Spring (May at West Grove, Pa.).

*Arrangement.*—Freely flowering, face outwards, hose-in-hose arranged at terminals with commonly approximately four to five flowers per terminal in a cluster.

*General appearance.*—Star-shaped, baby pearl pink colored petals with some variation in color, and persistent.

*Flower diameter.*—Approximately 4 cm when fully open.

*Buds.*—Approximately 3 cm in length, approximately 1 cm in diameter, near Red-Purple Group 64D to Red-Purple Group 65C in coloration, and oblanceolate in configuration.

*Petals.*—Iridescent and satiny in appearance; relatively smooth; the corolla consists of five petals that are fused at the base to form a sympetalous corolla; spathulate and rounded; entire with a somewhat ruffled margin; approximately 1.5 cm in length; approximately 1 cm in width; on the upper surface the coloration varies from Red-Purple Group 68A to Red-Purple Group 62C to Red-Purple Group 62D to Red-Purple Group 74C with near white, near White Group 155B, at the base; and on the under surface the coloration varies from Red-Purple Group 62D to Red-Purple Group 68A with near white, near White Group 155B, at the base.

*Sepals.*—In a fully open flower the five sepals are petaloid and fused at the base giving rise to the hose-in-hose designation. The coloration of the sepals closely corresponds to that of the petals.

*Peduncles.*—Generally upright and flexible, approximately 1 cm in length, and Yellow-Green Group 144D in coloration with pubescence of near Yellow-Green Group 145D.

*Stamens.*—Six, and approximately 2.5 cm in length.

*Anthers.*—Oblong, approximately 2 mm in size, and Greyed-Orange Group 166A in coloration.

*Pistils.*—One, and approximately 1.5 cm in length.

*Stigma.*—Rounded, and Yellow-Green Group 150D in coloration.

*Style.*—Red-Purple Group 62D to Red-Purple Group 66C in coloration.

*Ovary.*—Varies from Green Group 141D to White Group 155C in coloration with heavy pubescence.

*Fruit.*—No fruit or seeds have been observed during observations to date.

Hardiness: Is hardy to at least U.S.D.A. Hardiness Zone No. 5 during observations to date.

Disease resistance: Exhibits average disease resistance for an evergreen Azalea.

Culture: Tolerates wet soils and clay soils. Also, the blossoms tend to be sturdy and to retain their attractive appearance even if inclement weather is encountered.

The new variety of the present invention has not been observed under all possible environmental conditions. Accordingly, there is the possibility that the phenotypic expression may vary with changes in the environment such as temperature, day length, light intensity, nutrition, and degree of watering without any variance in the genotype.

I claim:

1. A new and distinct variety of Azalea plant characterized by the following combination of characteristics:

(a) Forms sturdy and attractive clusters of double pearl pink hose-in-hose blossoms, (b) Forms dark green foliage on a plentiful basis that generally retains its coloration in the winter, (c) Forms a dense well-branched naturally mounding growth habit, (d) Exhibits excellent bud hardiness, and (e) Exhibits tolerance to wet soils and clay soils;

substantially as herein shown and described.

* * * * *

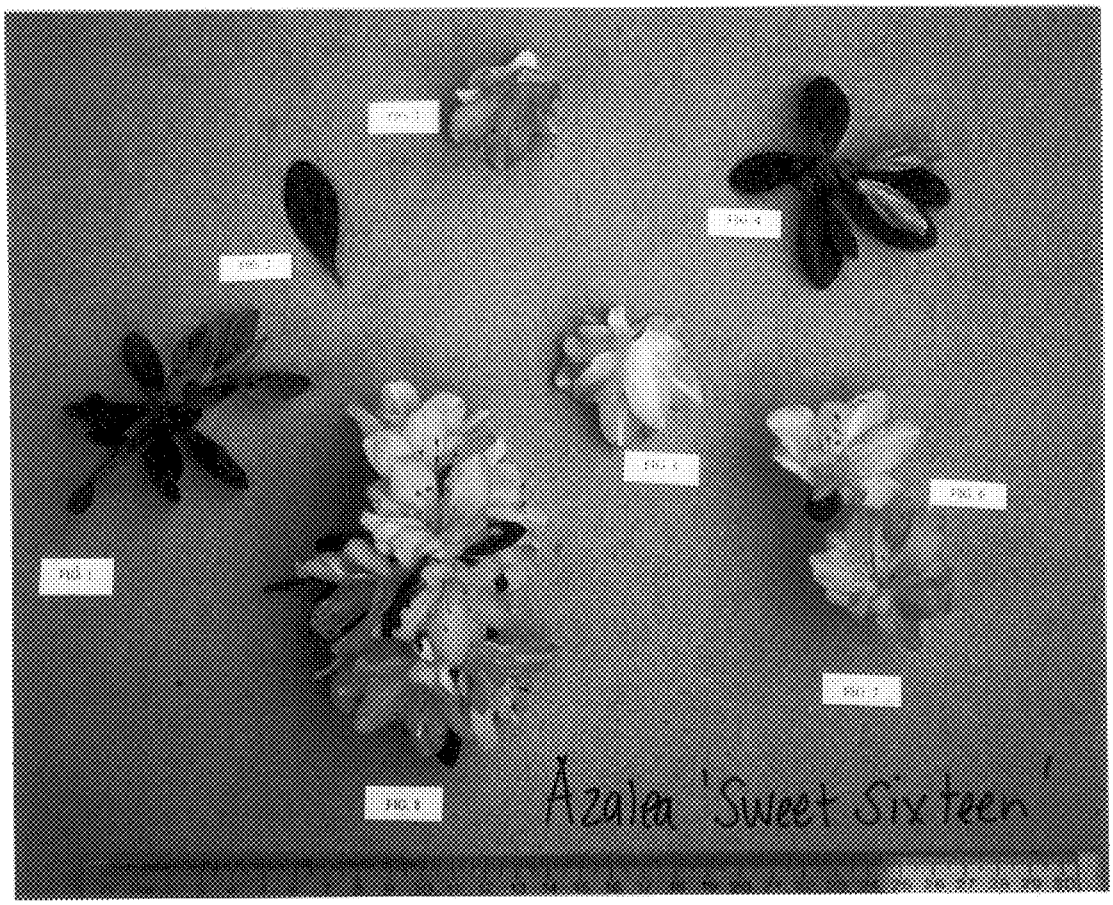
Azalea 'Sweet Sixteen'

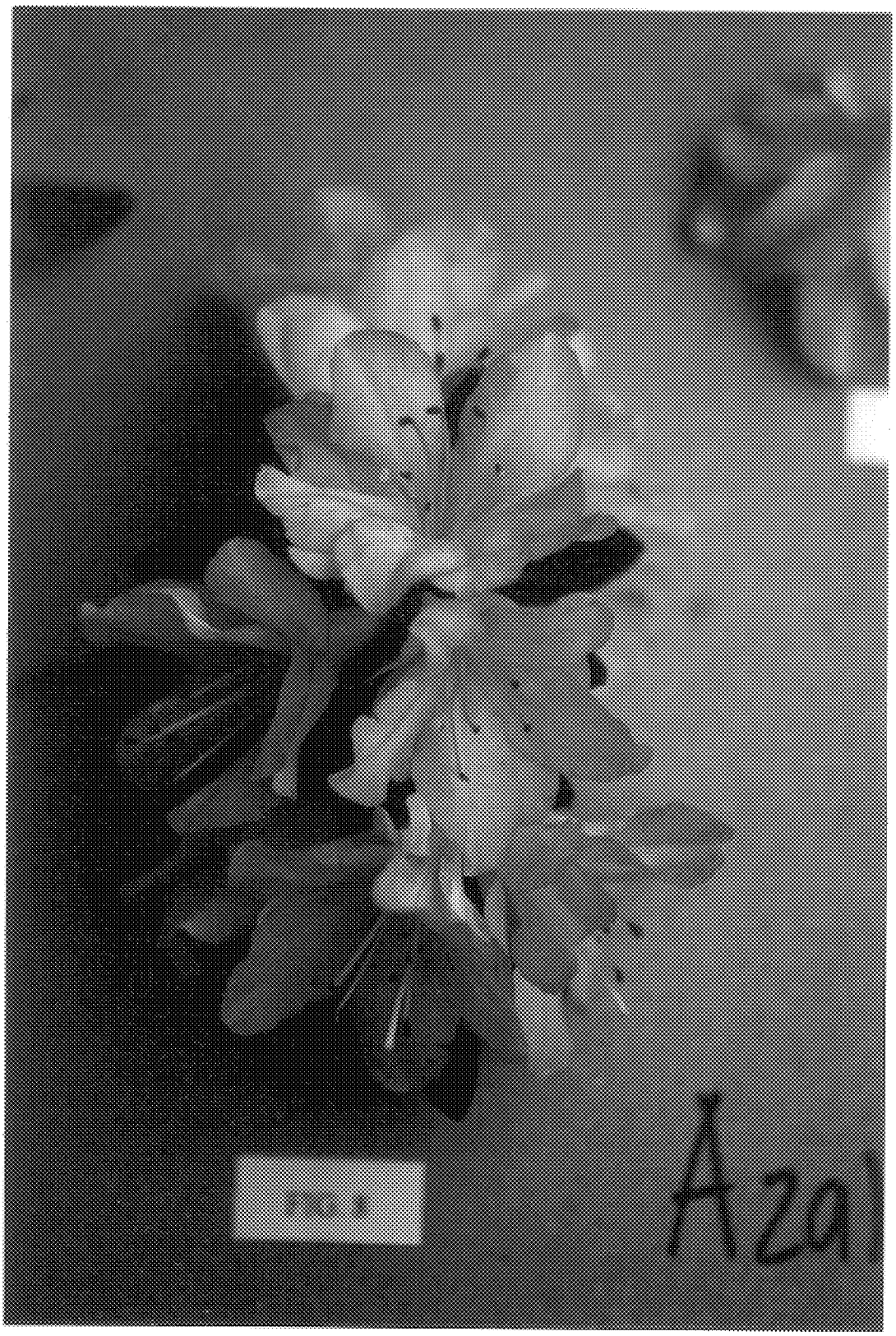
Azal